United States Patent [19]

Anderson

[11] Plant 4,077

[45] July 12, 1977

[54] GRAPEVINE

[76] Inventor: Frederic W. Anderson, 826 W. 22nd St., Merced, Calif. 95340

[21] Appl. No.: 727,159

[22] Filed: Sept. 27, 1976

[51] Int. Cl.[2] ..... A01H 5/03
[52] U.S. Cl. ..... Plt./47
[58] Field of Search ..... Plt./47

*Primary Examiner*—Robert E. Bagwill
*Attorney, Agent, or Firm*—Roger B. Webster

[57] ABSTRACT

A grapevine, of the Thompson Seedless class and adapted for like uses, which is of medium vigor, medium in trunk size, foliated with medium size cordate leaves having five lobes, blooming mid-season with fertile flowers, and productive to medium productive on medium length, straight canes of early ripening, medium size, single-shouldered, tapering clusters of seedless berries having excellent keeping quality and very good shipping quality.

1 Drawing Figure

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit, including grapevines. The present variety of grapevine resulted from my endeavors in the conduct of such plant breeding program.

ORIGIN OF THE VARIETY

The present variety of grapevine was originated by me, in my experimental nursery and orchard located as aforesaid, as a cross of Red Malaga (unpatented) as the seed parent, and the Thompson Seedless (unpatented) as the pollen parent. In maturity, such cross evidenced certain novel and distinctive characteristics desirable for a commercially grown grapevine, and I, therefore, undertook asexual reproduction of it preparatory to introduction to the trade.

ASEXUAL REPRODUCTION OF THE VARIETY

Subsequent to origination and selection by me of the present variety of grapevine, in the manner above described, I asexually reproduced it by cuttings and grafting, and — in maturity — such reproductions ran true to the original grapevine in all respects.

SUMMARY OF THE VARIETY

The present variety of grapevine, of the Thompson Seedless class and adapted for like uses, is of medium vigor, medium in trunk size, foliated with medium size cordate leaves having five lobes, blooming mid-season with fertile flowers, and productive to medium productive on medium length, straight canes of early ripening, medium size, single-shouldered, tapering clusters of seedless berries having excellent keeping quality and very good shipping quality; the variety, in comparison to the Thompson Seedless resembles the same in most respects, but ripens about 2 weeks earlier, and, in comparison to the Perlette (unpatented), has larger and more open clusters with more uniform size of the berries, and ripens about 1 week earlier.

BRIEF DESCRIPTION OF THE DRAWING

The drawing is an illustration, by photographic reproduction in color, of leaves, a cluster of berries, and separate berries, one of the latter being cut into halves to expose the flesh.

DESCRIPTION OF THE VARIETY

The botanical details of this new and distinct variety of grapevine — with color definitions (except those in common color terms) referenced to Maerz and Paul Dictionary of Color — are as follows:

Vine:
- *Vigor.*—Medium.
- *Productivity.*—Medium to productive.

Trunk:
- *Size.*—Medium.

Canes: Medium length; medium caliber; straight.
- *Nodes.*—Enlarged; flattened.
- *Internodes.*—Medium length.
- *Tendrils.*—Intermittent; medium thickness; medium length; bifurcated; smooth.

Flowers: Fertile.
- *Blooming Period.*—Mid-season; medium, as compared to other varieties.
- *Stamens.*—Upright.

Leaves: Medium size; average length — 6¼"; average width — 5"; cordate; medium thickness.
- *Color.*—Upper surface — medium green (23-L-9); dull. Lower Surface — Lighter green (22-G-7).
- *Texture of Upper Surface.*—Medium.
- *Lobes.*—Number — 5; terminal lobe — obtuse.
- *Petiolar Sinus.*—Medium depth; medium width.
- *Basal Sinus.*—Medium depth; medium width.
- *Lateral Sinus.*—Deep; medium width.
- *Margin.*—Serrate to dentate.
- *Teeth.*—Medium depth; medium width.

Fruit:
- *Date of Ripening.*—July 30–Aug. 5, 1976.
- *Season.*—Early.
- *Keeping Quality.*—Excellent.
- *Shipping Quality.*—Very good.
- *Cluster.*—Medium size; medium length; medium breadth; tapering; regular to irregular; single-shouldered; medium compactness.

*Peduncle.*—Medium length; medium thickness.

*Pedicel.*—Medium length; medium thickness.

*Brush.*—Medium length; yellow.

*Berries.*—Strongly adherent; medium size; average length — ⅔"; average width — ⅝"; uniform; oval.

*Color.*—Piquant green (20-K-6) with amber-yellow shading, with thin bloom.

*Skin.*—Medium thickness; medium texture; separates from pulp.

*Flesh.*—Pale green (20-F-4); translucent; meaty to medium; tender; juicy — clear; sweet to subacid; vinous; quality — good.

*Seeds.*—None, although sometimes a rudimentary but edible seed form exists.

*Use.*—Dessert; kitchen; market; home; raisin; wine.

The grapevine and its fruit herein described may vary in slight detail due to climatic and soil conditions under which the variety may be grown; the present description being of the variety as grown in the Central Valley of California.

I claim:

1. A new and distinct variety of grapevine, of the Thompson Seedless class, substantially as illustrated and described, which is of medium vigor, medium in trunk size, foliated with medium size cordate leaves having five lobes, blooming mid-season with fertile flowers, and productive to medium productive on medium length, straight canes of early ripening, medium size, single-shouldered, tapering clusters of seedless berries having excellent keeping quality and very good shipping quality; the variety, in comparison to the Thompson Seedless resembles the same in most respects, but ripens about 2 weeks earlier, and, in comparison to the Perlette, has larger and more open clusters with more uniform size of the berries, and ripens about 1 week earlier.

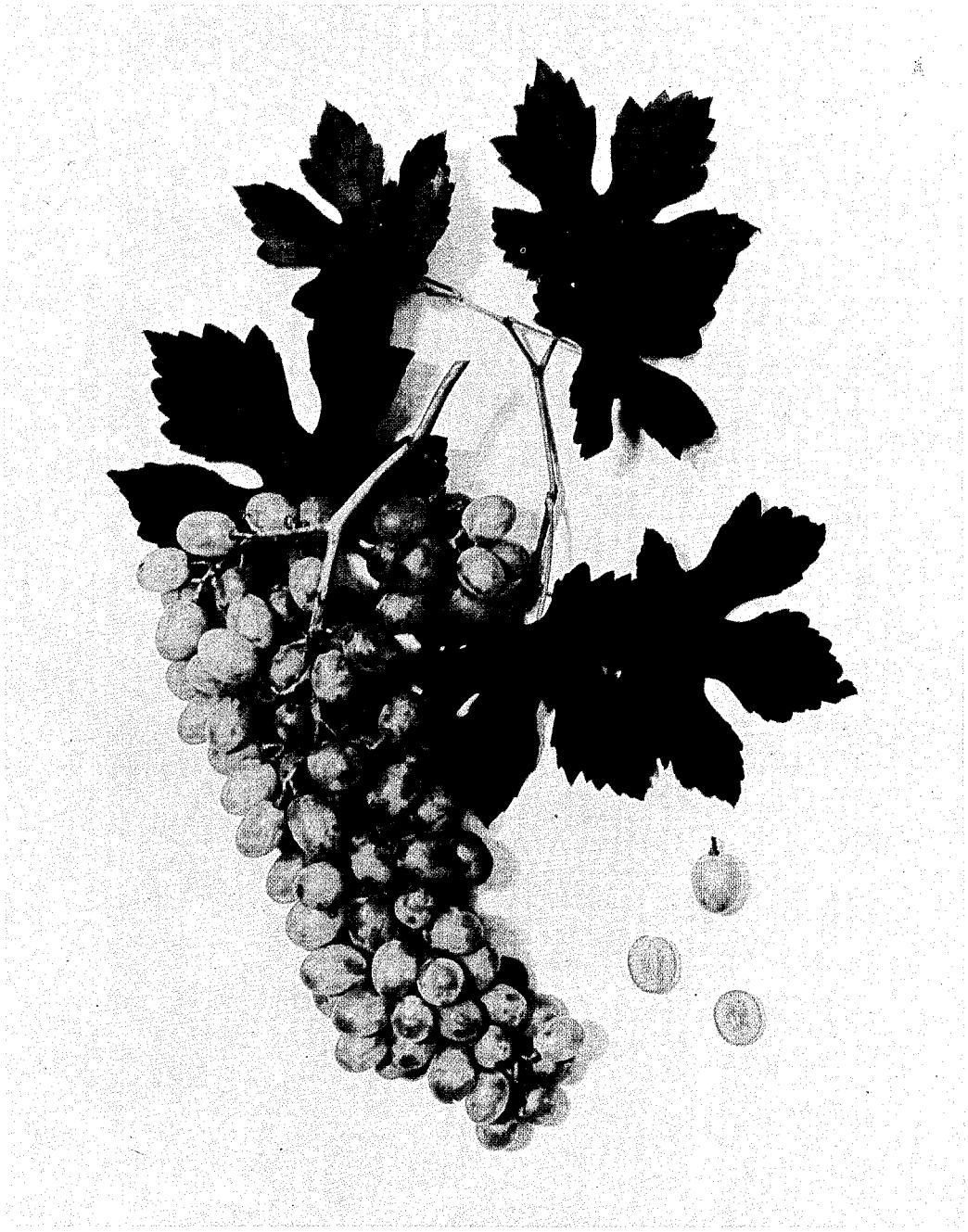

* * * * *